(12) United States Patent
Dam

(10) Patent No.: US 8,091,442 B1
(45) Date of Patent: Jan. 10, 2012

(54) POSITIVE TUBE RETENTION ARRANGEMENT

(75) Inventor: Naim Dam, Muttontown, NY (US)

(73) Assignee: Cosense, Inc., Hauppauge, NY (US)

( * ) Notice: Subject to any disclaimer, the term of this patent is extended or adjusted under 35 U.S.C. 154(b) by 869 days.

(21) Appl. No.: 12/148,430

(22) Filed: Apr. 19, 2008

(51) Int. Cl.
*G01N 29/02* (2006.01)

(52) U.S. Cl. ...................................... 73/866.5; 73/19.03

(58) Field of Classification Search ................ 73/19.03, 73/866.5, 432.1
See application file for complete search history.

(56) References Cited

U.S. PATENT DOCUMENTS

| | | | | |
|---|---|---|---|---|
| 3,921,622 A | * | 11/1975 | Cole | 600/437 |
| 5,537,853 A | * | 7/1996 | Finburgh et al. | 73/19.03 |
| 6,142,008 A | * | 11/2000 | Cole et al. | 73/19.03 |
| 6,622,542 B2 | * | 9/2003 | Derek et al. | 73/19.03 |
| 7,805,978 B2 | * | 10/2010 | Riley et al. | 73/19.03 |

* cited by examiner

*Primary Examiner* — Hezron E Williams
*Assistant Examiner* — Rose M Miller
(74) *Attorney, Agent, or Firm* — Gordon D. Coplein

(57) ABSTRACT

A measuring head has a base and extending spaced apart vertical sidewalls that form a slot into which a tube through which a fluid flows is placed and at least one sensor element mounted in at least one of the sidewalls to detect a characteristic of the flowing fluid. At least one through passage is formed in each of the sidewalls that are aligned opposing each other to form a pair of passages through which a strap is passed above the tube in the head slot and a fastener holds the strap bound to the sidewalls to retain the tube in the slot. One embodiment has a pair of the sidewall slots on each side of a sensor element mounted in a sidewall. A passage also can be provided in the head base through which a strap can pass and then be passed through a pair of the sidewall passages.

17 Claims, 7 Drawing Sheets

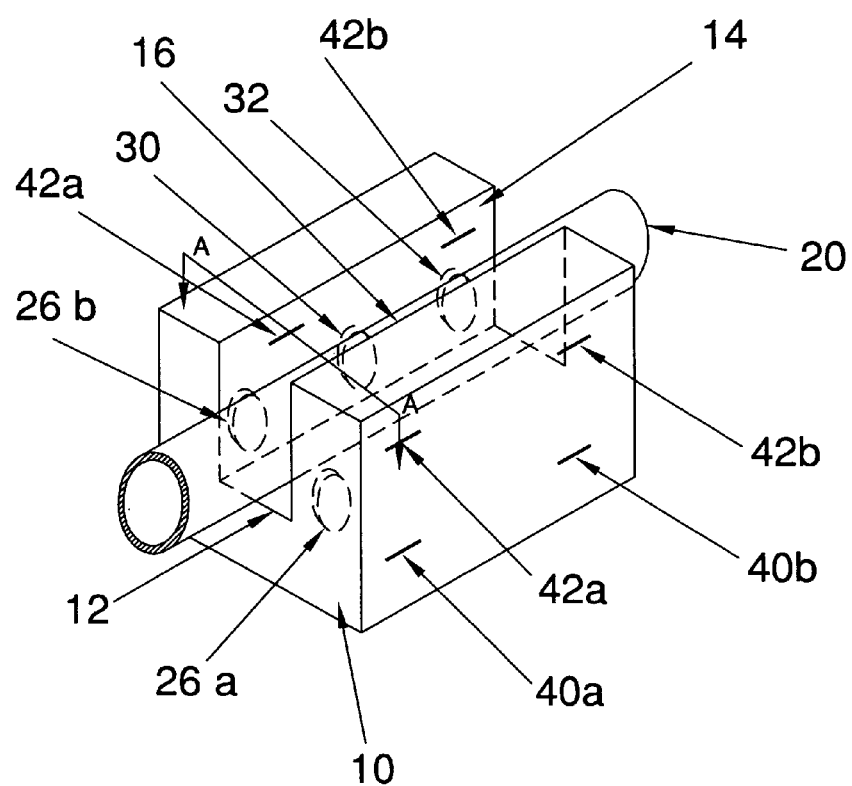
FIG: 1

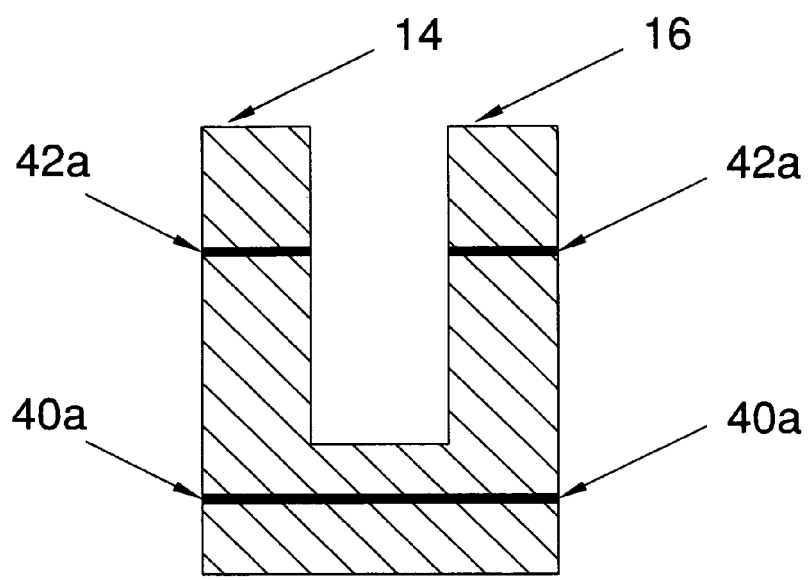
FIG: 1A

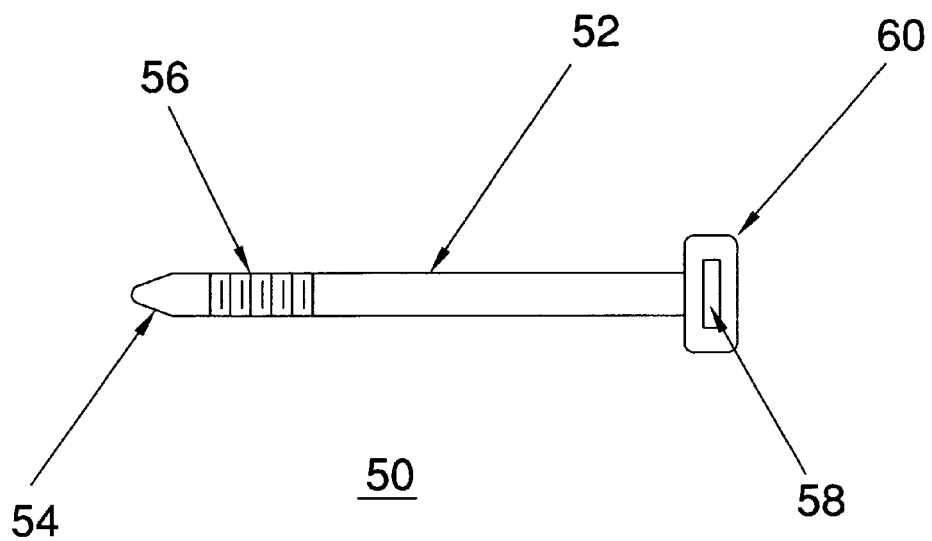
FIG: 1B

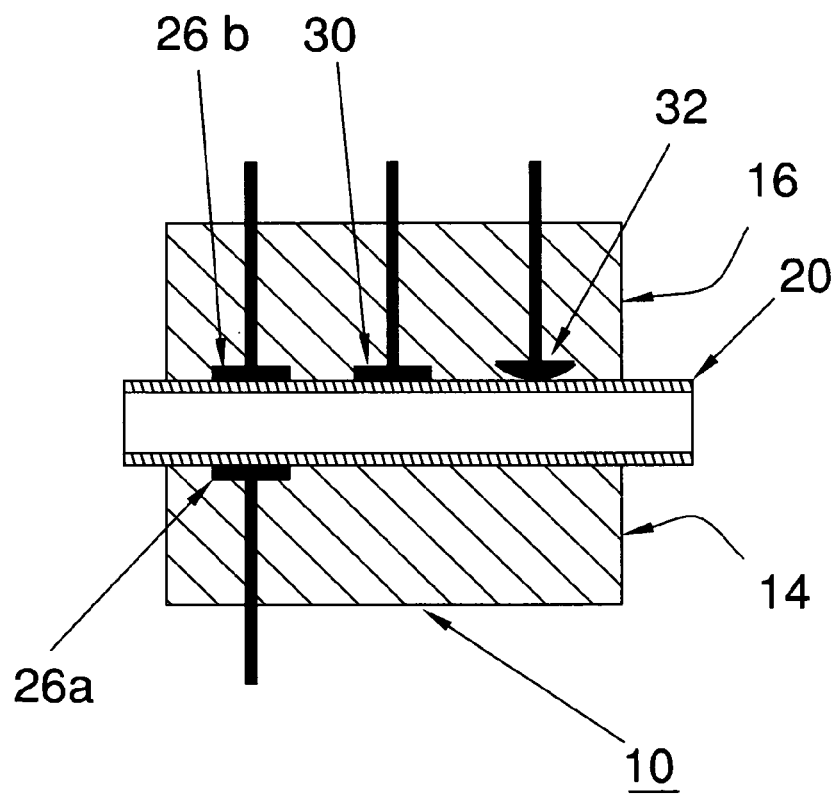
FIG: 2

POSITIVE TUBE RETENTION ARRANGEMENT

FIELD OF THE INVENTION

The present invention relates to apparatus for securely maintaining a tube with a flowing liquid in a head that contains one or more sensors to determine various characteristics of a liquid flowing in the tube.

BACKGROUND OF THE INVENTION

In pending application Ser No. 11/903,261, filed Sep. 21, 2007, titled "Non-Invasive Multi-Function Sensor", the disclosure of which is incorporated herein by reference, a system is disclosed for measuring various characteristics of a liquid flowing in a tube of a compressible material, such as of plastic. These characteristics can be, for example, one or more of the temperature of the liquid as measured by a temperature sensor, the presence of air bubbles or particles in the liquid as measured by an ultrasonic sensor, and the type of liquid as measured by color determination using an LED. Such a system, or one or more parts of it, is found to be useful in medical and analytical laboratories where, for example, an end user needs to know if air bubbles or particles are present in the liquid. Such a system also could let a user know the presence/absence of a liquid flowing in the tube for fill and empty applications of various liquids and solutions in semi-conductor industries.

The system of the applications uses a measuring head that contains, depending on the application and requirements, one or more of the sensors for making the determination of the characteristic or characteristics of the liquid. The head has a slot in which the tube of compressible material is placed to be confronted by the sensing element or elements of each of the one or more sensors. For example, an ultrasonic sensor used to determine the presence of air bubbles/particles and the presence or absence of liquid in the tube would have two elements such as a piezoelectric crystals, one for transmitting energy through the tube and the other for receiving the energy. These crystals are on opposite walls of the slot in which the tube is placed.

In the measuring head of the system as described in the application it has been determined that it would be advantageous to provide an arrangement for positively holding or locking the tube in the slot. This is of importance while measurement of the liquid characteristics is taking place to prevent the tube from becoming displaced from the slot if the head out to is accidentally moved. It is preferred that such a positive locking arrangement be simple and easy to use and also inexpensive in its construction.

BRIEF DESCRIPTION OF THE INVENTION

In accordance with the invention, a measuring head for a system that is to determine one or more characteristics of a liquid flowing in a tube of compressible material has a slot in which the tube is placed. The measuring head has one or more sensors mounted in the walls that form the slot to sense characteristics of the liquid. In accordance with the invention the measuring head is provided with a positive locking arrangement to keep the tube in place in the slot The locking arrangement also provides for a positive insertion of the tube in the slot so as to align it with the sensor elements such as the ultrasonic crystals used for sensing particles and air bubbles so that there will be a proper transmission and reception of the ultrasonic energy. The locking arrangement also functions to provide proper positioning for other types of sensors such as an LED and a temperature detector.

The locking arrangement includes providing the measuring head to have passages through which a locking strap can be passed and to be able to be pass over the part of the tube in the slot that is exposed and to hold the tube in place. The passages through which the strap passes can be only in the head walls forming the slot above the tube, only in the base of the head below the tube, or a combination of both. This permits the strap to encompass the tube in a variety of ways. The locking strap preferably is of a flexible material such as plastic or thin metal that has a flat face to oppose the tube. One end of the strap passes though a passage in the head and a fastener is provided at the other end. One suitable form of a strap is in the form of a cable tie that has a locking head at one end through which the strap other end passes to be locked within the locking head. The strap preferably engages the tube in the measuring head slot while liquid is flowing through the tube to firmly hold it in place although it can be somewhat above the tube and not engage it. The invention provides a positive lock for the tube in the slot that is simple to operate and that is highly effective.

BRIEF DESCRIPTION OF THE DRAWINGS

Other objects advantage of the present invention will become more apparent upon reference to the following specification and annexed drawings in which:

FIG. 1 is a perspective view of a typical measuring head including a portion of the invention;

FIG. 1A is a cross-sectional view along the lines A-A of FIG. 1;

FIG. 1B is a top plan view of one form of a fastener;

FIG. 2 is a top view of the measuring head of FIG. 1;

DETAILED DESCRIPTION OF THE INVENTION

Figure 3:
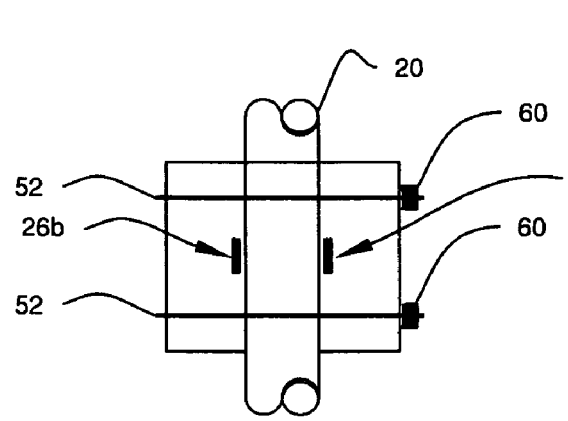
FIGS. 3 and 3A are top and end views of a first embodiment of use of the strap.

FIGS. 1 and 2 show an integral multi-function sensor measuring head according to the prior application. While the strap locking invention of the present invention is described with respect to a multi-function measuring ahead, the measuring head can contain only one sensor to perform only a single function. The head 10 is shown as a generally rectangular block that is preferably of a plastic material such as UDEL polysulfone resin manufactured by Solvay Advanced Polymers. The head 10 can be molded or made by any other suitable technique. In the head 10 there is a longitudinal slot 12 that has opposing sidewalls 14 and 16. A tube 20 of flexible and elastically outwardly expansible plastic material having a liquid flowing in it is to be placed in the slot 12 and is shown. In a typical medical type application the tube 20 is to have one end connected to the body of a patient and the other end connected to a liquid supply, such as a medicine or saline solution, or to a machine such as a dialysis machine. In a manufacturing application one end of the tube would be connected to a supply of a liquid which exits through the other end to a desired point.

In the making of the head 10 a number of depressions are formed on the inner faces of the opposing slot sidewalls 14 and 16. Different types of sensor elements, to be described below, are mounted in the depressions and each depression is of a shape to accommodate the particular type of sensor element that is mounted in it. The slot sidewall thickness is typically 0.30" to 0.050" depending upon plastic material and the sensor elements used. A hole is drilled through the outside wall of the head 10 to each of the depressions in the slot sidewalls 14 and 16 to accommodate a respective lead wire or wires connected to the respective sensor element.

Considering the sensor elements, near one end of the head 10 is a pair of piezoelectric elements, or crystals, 26a and 26b mounted opposing each other in the slot opposing slot sidewalls 14 and 16. The piezoelectric elements 26a and 26b are of any suitable material used in ultrasonic technology, such as PZT or PVDF material. Near the center of the head 10 a temperature sensor 30 is mounted in one of the slot sidewalls 14 and a force sensor (not shown) can be mounted in the other sidewall 16. Near the other end of the is e head 10 a light emitting element 32, such as an LED, is mounted in the sidewall 14 and a photodetector (not shown) is mounted opposing it in the sidewall 16. The representation of the shapes of the various sensor elements are in schematic form and the shape will depend upon the specific sensor element that is used. The placement of the various sensor elements also can be varied. Each of the sensor elements is held in its respective depression by a suitable adhesive, such as an epoxy, and the lead wires for each sensor element pass out through the walls of the head that form the slot to be exterior of the head so as to be able to be connected to a suitable electronic circuit.

In the operation of the system of the invention, the plastic tube 20 is laid in the slot 12 of the head 10. In some cases, depending upon the material of the tube, the tube can expand when liquid is flowing through it. The width of the slot 12 preferably is about the same or slightly less than the outer diameter of the plastic tube 20 in its relaxed state so that the faces of the sensor elements 26, 28 and 30 mounted in the opposing slot sidewalls 14 and 16 that need to be in contact with the tube 20 makes such contact. A typical deformation or squeeze of the tube in the slot would be 15% to 20% of the tube outer diameter. That is, it will tend to expand from a circular to a somewhat elliptical shape. The light emitting element 32 and photo transistor optical elements need not necessarily make contact with the wall of the plastic tube but one or both of these elements can make such contact. A description of individual sensor elements and their respective functions follows.

The piezoelectric elements 26a and 26b are to operate as part of an air bubble/particle detection and characterization apparatus. In such an apparatus, ultrasonic energy is supplied to one of the piezoelectric elements 26 and is transmitted though the tube 20 to be received by the other element. A circuit of this type is described in U.S. patent application Ser. No. 11/703,025, filed Feb. 7, 2007 for "Ultrasonic System for Detecting and Quantifying of Air Bubbles/particles in a Flowing Liquid", which is assigned to the assignee of this application and whose disclosure is incorporated herein by reference.

The temperature sensor element 28 preferably is an infrared thermocouple, an example being P/N: 150042, Model No C UIRT-K-98.6f/37C manufactured by Exergen, Watertown, Mass. This device has the ability to measure the internal temperature of the liquid in the tube 20 non-invasively by measuring both tube surface temperature and the ambient temperature. It is preferred that the sensor element 28 is mounted in the head 10 so as to converge the sensor infrared beam at a focus point in the middle of tube 20 to measure fluid temperature accurately.

Referring to FIGS. 1 and 1A, to form a secure lock for the tube 20 in the slot 12 spaced lower passages 40a and 40b extend through and across the base of the head 10 from one side to the other for a locking strap to pass through. Upper passages 42a and 42b are formed through each of the sidewalls 14 and 16 each preferably generally aligned vertically with a corresponding lower passage 40a and 40b. The upper opposing passages 40a in the two sidewalls 14 and 16 form one pair of upper passages and the opposing sidewall passages 40b form a second pair. The passages 40 and 42 are shown as being generally rectangular but they can be of any other desired shape, such as circular, depending upon the shape of the locking strap to be used. The passages 40 and 42 can be formed by any suitable technique such as drilling, milling, machining or using a heat lance. For some embodiments of the invention the passages 40 and 42 also can be formed by cutting out a portion of the head 10. For example, to form an upper passage 42 an open slot can be made in each sidewall from its top down to a position above the tube 20. The lower passages 40 can be made by cutting slots across the width of the base of head 10.

Two sets of passages 40a-42a and 40b-42b are illustratively shown along the length of the head 10 in FIG. 1 and a sensor such as formed by the elements 26a and 26b is placed between the two sets. There can be only one or three or more sets as appropriate for the application relative to the size of the tube, degree of locking security needed for the tube, and the number of sensors in the measuring head 10. Also, in some of the embodiments of the invention, as described below, only the upper passages 42 have to be provided.

It is preferred that the strap have a flat face that faces the tube in the slot. FIG. 1B shows one form of locking strap 50 that can be used with the invention. This is in the form of a plastic cable tie having an elongated piece 52 which is tapered and pointed at one end 54. A fastener for the strap 50 is provided by the elongated piece 52 having a plurality of ridges 56 along all or a portion of its length. At the other end of the piece 52 is a square or rectangular head 60 with an opening 58 into which the pointed end 54 of the piece 52 is inserted. Within the head 60 are a plurality of mating ridges (not shown) that lock with the ridges 56 on the elongated piece 52 upon the piece 52 engaging an object and being pulled through the head 60. A flat and flexible piece of metal, such as the legs of a fastener base used with a file also can be used as the strap.

Figure 3A:
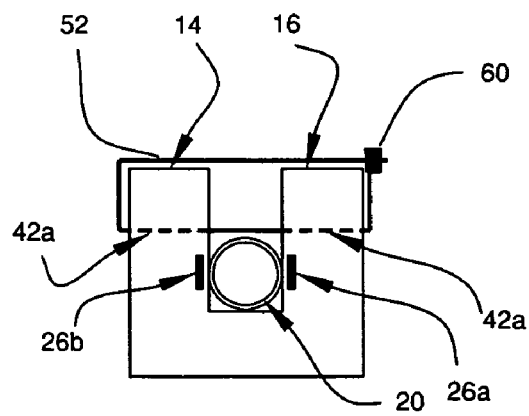

FIGS. 3 and 3A show one embodiment of how positive tube retention is accomplished by the invention using the cable tie of FIG. 1B and only the upper passages 42 of the measuring head 10. As seen best in FIG. 3A the elongated piece 52 of the strap 50 is passed through the passages 42a in the sidewalls 14 and 16. It is preferred that the flat face of the strap elongated piece 52 slightly engage the top of the tube 20 when it is in its normal expanded state with liquid flowing through it. The strap preferably should not compress the tube and thereby restrict the liquid flow. The elongated piece 52 is looped over the top ends of the sidewalls with the end of the strap elongated piece 52 being placed in the head 60 and pulled tight engaging the upper ends and tops of the sidewalls 14 and 16. FIG. 3 shows two of the straps elongated pieces 52 in the head 10 one placed on each side of the piezoelectric crystals 26a and 26b, in this case, the head 10 having only the ultrasonic measuring sensor formed by the elements 26. The two straps 50 positively lock the tube 20 in the slot 12 of the head 10 so that during performance of the application taking place the tube 20 will be retained positioned in the head slot 12 if the head or tube is moved or even if the head is turned upside down. In the case of the strap being formed by a thin piece of metal, the ends of the strap would be bent together after looping around the tops of the sidewalls and possibly also crimped together by a suitable tool.

Figure 4:
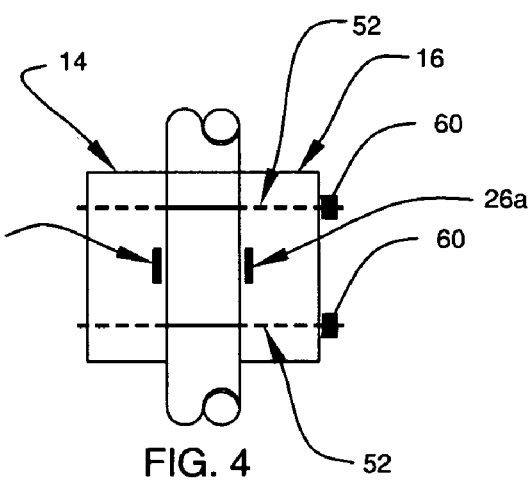
FIGS. 4 and 4A are top and end views of a second embodiment, showing use of the strap.
Figure 4A:
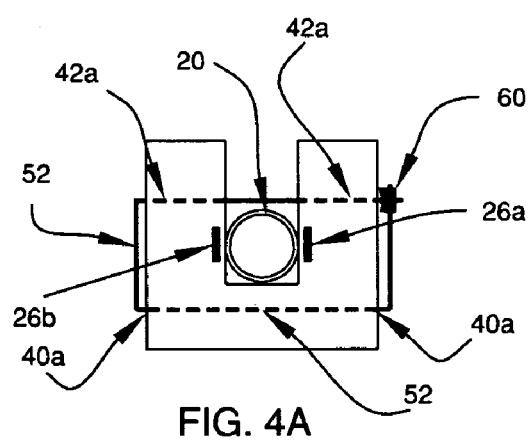

FIGS. 4 and 4A show a second embodiment of the invention in which the strap 50 elongated piece 52 is passed through the lower passage 40 in the base of the head and then through the passages 42 in the sidewalls 14 and 16 with the flat face of the strap elongated piece 52 facing the tube 20 underneath it to hold the tube within the slot 20. Again, FIG. 4 shows two of the straps, one on each side of the piezoelectric crystals 26a and 26b.

Figure 5:
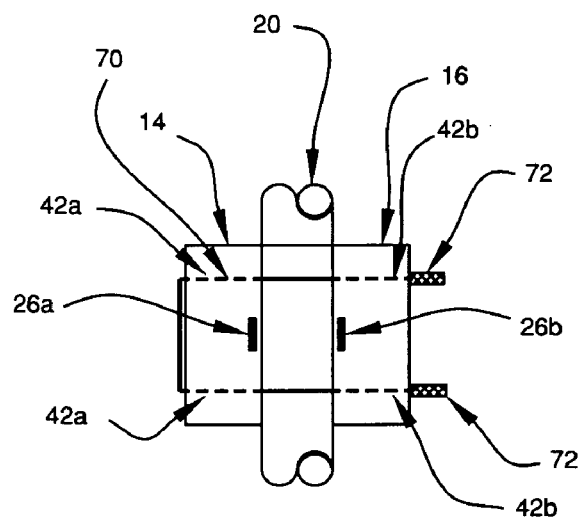
FIGS. 5 and 5A are top and end views of a third embodiment of the invention showing use of the strap.
Figure 5A:
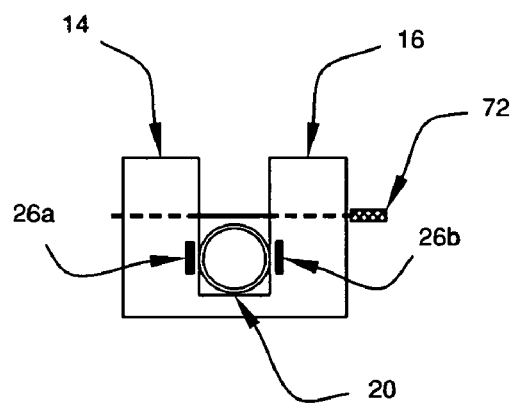

FIGS. 5 and 5A show another embodiment in which the locking strap 70 is of metal or plastic that has a thread at each end on which a nut 72 can be fastened. The strap 70 can be flat or round so long as its ends are formed to have threads to accept the nut 72. If the strap is flat, it can be bent at 90° where it enters or exits the passages 42 on the sidewall 14 so that a flat elongated piece faces the tube 20 in the slot. In this embodiment a single strap 70 is passed through only the passages 42a and 42b in the sidewalls 14 and 16 to form a C-shape such that the single strap overlies the tube 20 at two places, one on each side of the piezoelectric elements 26a and 26b. Again, it is preferred that the strap 70 just engage the top of the expanded tube 20. The strap 70 also can be of a generally square configuration so that it will have a flat face to oppose the tube 20. In this case, the passages 42 would be of a shape to accommodate that of the strap 70.

Figure 6:
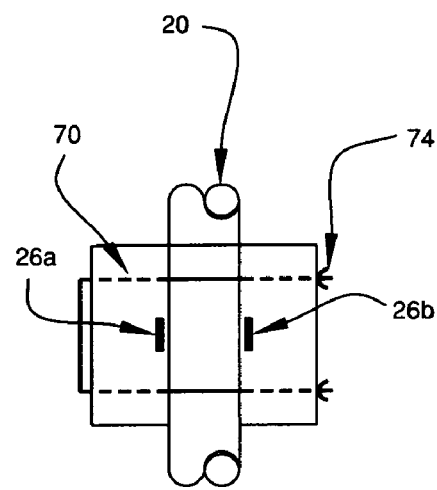
FIGS. 6 and 6A are top and end views of a fourth embodiment of the invention.
Figure 6A:
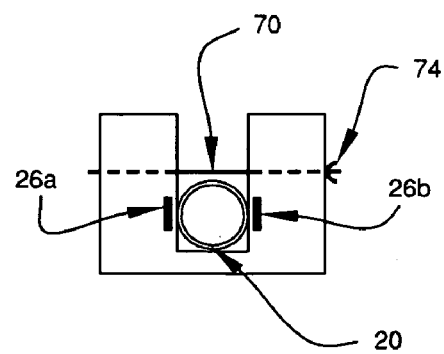

FIGS. 6 and 6A show another embodiment of the invention, which is similar to that of FIGS. 5 and 5A. Here, a threaded or split ring engaging and gripping type retaining washer 74 is used at each end of the strap 70 to provide a larger area of surface contact against the outside of the sidewall at each end of the strap 70.

Figure 7:
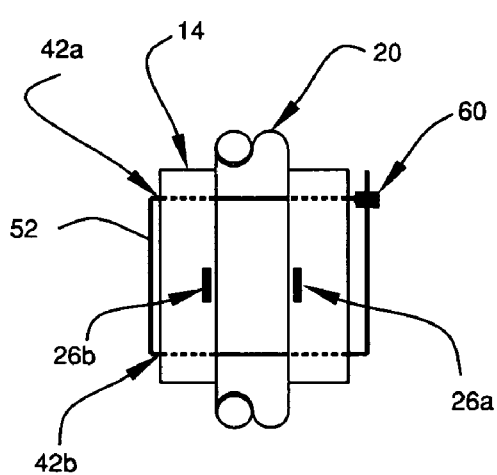
FIGS. 7 and 7A are top and end views of a fifth embodiment of the invention.
Figure 7A:
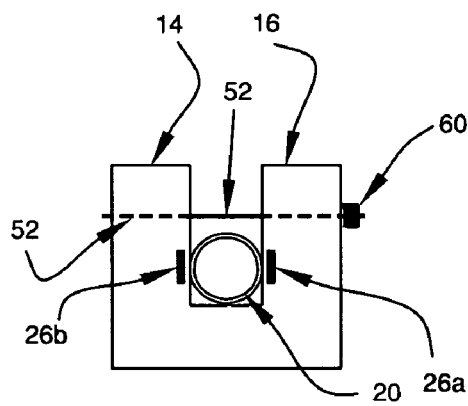

FIGS. 7 and 7A show yet a further embodiment of the invention in which the strap 50 or a wire is passed through each of the two pair of upper passages 42a and 42b in the sidewalls 14 and 16 to produce a generally rectangular or square configuration for the strap. Here a flat strap would be bent at a 90° angle as it enters and exits the upper passages 42 of the sidewalls so that a flat face of the strap will oppose the tube. As see two parts of the same strap overlie the tube 20, one part one on each side of the piezoelectric element 26.

Figure 8:
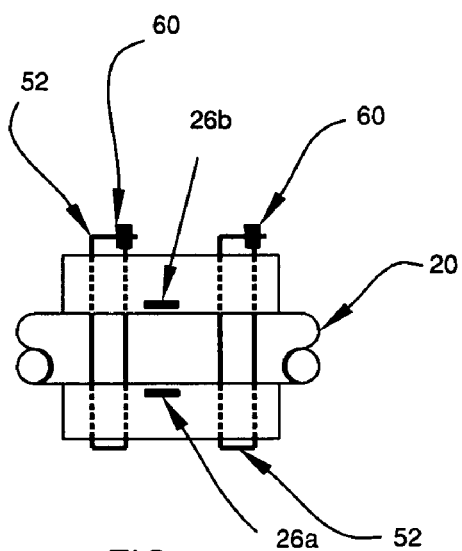
FIGS. 8 and 8A are top and end views of a sixth embodiment of the invention
Figure 8A:
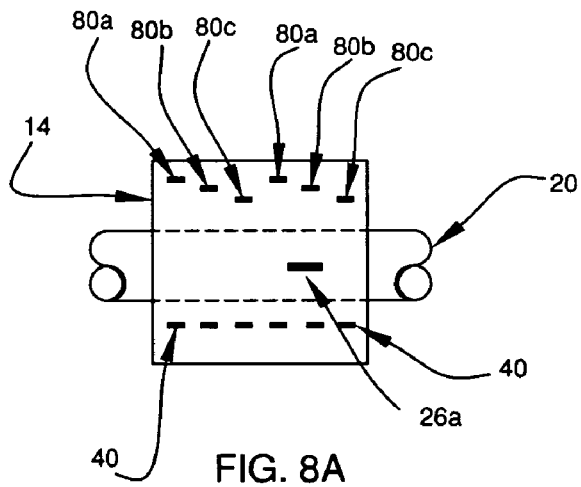

In the embodiment of FIGS. 8 and 8A a number of the through passages 40 are formed spaced apart in the base of the head across its length. In each of the sidewalls 14 and 16, sidewall 14 being shown in FIG. 8A, two sets of upper through passages 80a, 80b and 80c are formed. Each sidewall passage 80 is vertically aligned above a corresponding base passage 40. The passages 80 of a set are stepped apart in increasing vertical height, or distance, above a corresponding lower passage 40. The vertically stepped passages 80 provide for the head 10 to accommodate different size tubes 20 and still being able to have the straps 50 or 70 come into contact with the tube to hold it securely in the slot. The piezoelectric sensor 26 is centered between the two sets of passages 80. The strapping arrangement shown in FIGS. 4 and 4A is shown in which one strap passes through a set of the upper and lower passages 40 and 42 on each side of the sensor 26. However, any of the strapping arrangements of FIGS. 3-7 previously described can be used with the embodiment of FIGS. 8 and 8A. That is, only the upper passages 80 have to be provided.

Specific features of the invention are shown in one or more of the drawings for convenience only, as each feature may be combined with other features in accordance with the invention. Alternative embodiments will be recognized by those skilled in the art and are intended to be included within the scope of the claims. Accordingly, the above description should be construed as illustrating and not limiting the scope of the invention. All such obvious changes and modifications are within the patented scope of the appended claims.

I claim:

1. The combination comprising:
   a measuring head having a base from which extends spaced apart vertical sidewalls to form a slot between said sidewalls into which a tube through which a fluid flows can be placed, and at least one sensor element mounted in at least one of said sidewalls for use in detecting a characteristic of the fluid flowing in the tube;
   at least one through passage in each of said head sidewalls with two of said passages being aligned opposing each other to form at least one pair of passages;
   a strap to pass through at least one pair of the aligned opposing sidewall passages above the tube in the head slot;
   and at least one fastener for said strap to hold said strap bound to said sidewalls.

2. The combination of claim 1 wherein each of the ends of said strap extends through at least one of a respective pair of said aligned opposing sidewall passages and there is a fastener at each of said ends to engage a respective sidewall.

3. The combination of claim 2 wherein each end of said strap is threaded and each fastener comprises a nut.

4. The combination of claim 2 wherein the fastener at each end of said strap comprises a retaining washer.

5. The combination of claim 1 wherein said strap wraps over the top ends of both said sidewalls.

6. The combination of claim 5 wherein said strap comprises a cable tie having a first part that overlies the tube in the slot, a second part that wraps over the top ends of both of said sidewalls, and a head through which the free end of said cable tie passes to be locked in said cable tie head.

7. The combination of claim 1 wherein the at least one through passage in each sidewall comprises two passages in each sidewall spaced apart to form two of said aligned opposing pairs of said passages and the at least one sensor element is between said two passages in one single sidewall, and wherein said strap comprises two straps and said at least one fastener comprises at least two fasteners, with one strap and at least one fastener for each said pair of opposed aligned opposing sidewall passages.

8. The combination of claim 1 wherein the at least one through passage in each sidewall comprises two passages in each sidewall spaced apart to form two of said pairs of said aligned opposing passages and the at least one sensor element is between said two passages in one single sidewall, the strap comprises a single strap that passes though all of said passages of said two pair of aligned opposing passages, and said at least one fastener is at the ends of the strap.

9. The combination of claim 1 wherein the at least one through passage in each sidewall comprises two passages in each sidewall spaced apart to form two of said aligned opposing pairs of said passages and the at least one sensor element is between said two passages in one single sidewall, said strap comprises a single strap that passes though all of said passages of said two pair of aligned opposing passages, and the at least one fastener comprises a fastener at each of the ends of the strap to engage the same sidewall outer face.

10. The combination of claim 1 further comprising at least one through passage in the base of said head below said slot that is generally aligned with each of said passages of a single pair of aligned opposing passages in said opposing sidewalls and wherein said strap passes through said base passage and a said pair of aligned opposing sidewall passages.

11. The combination of claim 10 wherein said strap comprises a cable tie having a head through which the free end of said cable tie passes to be locked in said cable tie head.

12. The combination of claim 10 wherein the at least one through passage in each sidewall comprises two passages in each sidewall spaced apart to form two of said pairs of aligned opposing passages and the at least one sensor element is between said two passages of at least in one single sidewall, the at least one base passage comprises a respective through passage in the base of said head below each said pair of aligned opposing sidewall passages, each said respective base passage being generally aligned with each said pair of sidewall passages, and said strap comprises two straps, each strap passing through one said base passage and the corresponding aligned opposed pair of sidewall passages.

13. The combination of claim 12 wherein each said strap comprises a cable tie having a head through which the free end of said cable tie passes to be locked in said cable tie head.

14. The combination of claim 1 wherein the at least one through passage in each of said sidewalls comprises a set of vertically stepped through passages aligned opposing each other in each said sidewall to form corresponding set of pairs of aligned opposing sidewall passages.

15. The combination of claim 14 further comprising a respective through passage in said head base below each said pair of aligned opposing passages that is generally aligned with each of said aligned opposing sidewall passages of said respective pair, and said strap comprises at least one strap to pass through one said respective base passage and the corresponding pair of aligned opposed sidewall passages in said set.

16. The combination of claim 14 further comprising two sets of said vertically stepped pairs of aligned opposed through passages in each sidewall spaced apart with said at least one sensor element being placed between said two sets of vertically stepped passages in a single sidewall, and said strap and said fastener comprises one strap and at least one fastener for one pair of passages of each said set.

17. The combination of claim 16 further comprising a respective through passage in said head base below each said pair of aligned opposing sidewall passages of each said set of pairs of aligned opposing passages, said base passage being that is generally aligned with each pair of passages of the set, and said strap comprising at least one strap for each set of vertically stepped pairs, each strap passing through one said base passage and the corresponding pair of sidewall passages of the respective set of pairs of passages.

* * * * *